(12) United States Patent
Fuchs et al.

(10) Patent No.: US 6,291,673 B1
(45) Date of Patent: Sep. 18, 2001

(54) FOLIC ACID DERIVATIVES

(75) Inventors: Philip L. Fuchs; Jin Luo, both of West Lafayette; Douglas A. Lantrip, Lafayette, all of IN (US)

(73) Assignee: Purdue Research Foundation

( * ) Notice: Subject to any disclaimer, the term of this patent is extended or adjusted under 35 U.S.C. 154(b) by 0 days.

(21) Appl. No.: 09/529,682

(22) PCT Filed: Oct. 16, 1998

(86) PCT No.: PCT/US98/21914

§ 371 Date: Apr. 17, 2000

§ 102(e) Date: Apr. 17, 2000

(87) PCT Pub. No.: WO99/20626

PCT Pub. Date: Apr. 29, 1999

Related U.S. Application Data (60) Provisional application No. 60/062,009, filed on Oct. 17, 1997.

(51) Int. Cl.$^7$ ........................ C07D 475/04; C07D 475/08
(52) U.S. Cl. ........................ 544/260; 544/258; 544/260; 544/261
(58) Field of Search ........................ 544/258, 260, 544/261

(56) References Cited

PUBLICATIONS

Martinelli and Chaykovsky "Methotrexate Anolouges. 12. Synthesis and Biological Properties of Some Aza Homologues," *J. Med. Chem.*, vol. 22, No. 7, 1979, pp. 869–874.

Martinelli and Chaykovsky "Synthesis of Aza Homologues of Folic Acid" *J. Med. Chem.*, vol. 22, No. 7, 1979, pp. 874–877.

Rosowsky et al., "Methotrexate Analogues. 14. Synthesis of New y–Substituted Derivatives as Dihydrofolate Reductase Inhibitors and Potential Anticancer agents." *J. Med. Chem.*, vol. 24, 1981, pp. 1450–1455.

Wang et al. "Synthesis, Purification, and Tumor Cell Uptake of 67–Ga–Deferoxamine–Folate, a Potential Radiopharmaceutical for Tumor Imaging," *Bioconjugate Chem.*, 1996, vo. 7, pp. 56–62.

Danishefsky et al. "A Simple Synthesis of L–y–Carboxyglutamate and Derivatives Thereof" *J. Am. Chem. Soc.*, vol. 101, No. 15, 1979, pp. 4385–4386.

Temple et al. "Chemical and Physical Properties of Folic Acid and Reduced Derivatives" Folates Pterins, vol. 1, 1984, pp. 61–120.

Rosowsky et al. "Methotrexate Anolouges. 15. A Methotrexate Analogue Designed for Active–Site–Directed Irreversible Inactivation of Dihydrofolate Reductase,",*J. Med. Chem.*, vol. 25, 1982, pp. 960–964.

Chaykovsky et al. "Methotrexate Analogs. 6. Replacement of Glutamic Acid by Various Amino Acid Esters and Amines" *J. Med. Chem.*, vol. 18, No. 9, 1975, pp. 909–912.

Piper et al., "Synthesis of α–and y–Substituted Amides, Peptides, and Esters of Methotrexate and Their Evaluation as Inhibitors of Folate Metabolism." *J. Med. Chem.*, vol. 25, 1982, pp. 182–187.

Temple et al. "Chemical Conversion of Folic Acid to Pteroic Acid."*J. Org. Chem.*, vol. 46, 1981, pp. 3666–3667.

Collado et al. "Diastereoselective Functionalization of 5–Hydroxy Prolinates by Tandem Horner–Emmons–Michael Reaction" *Tetrahedron Letters.*, vol. 35, No. 43, 1994, pp. 8037–8040.

Dixit et al., "Facile Acid Catalyzed Ring Cleavage of N–Acylated Lactams." *Tetrahedron Letters*, vol. 35, No. 33, 1994, pp. 6133–6134.

*Primary Examiner*—John M. Ford
(74) *Attorney, Agent, or Firm*—Barnes & Thornburg (57) ABSTRACT

Novel folic acid derivatives and their use in preparation of γ-esters of folic acid via a pteroyl azide intermediate are described. Folic acid γ-esters are useful intermediates in the synthesis of folic acid conjugates capable of binding folate receptors in vitro and in vivo.

2 Claims, 9 Drawing Sheets

FOLIC ACID DERIVATIVES

CROSS-REFERENCES TO RELATED APPLICATIONS

This application is a U.S. national counterpart application of international application Ser. No. PCT/US98/21914 filed Oct. 16, 1998, which claims priority to U.S. provisional application Ser. No. 60/062,009 filed Oct. 17, 1997.

FIELD OF THE INVENTION

This invention relates to the preparation of folic acid derivatives. More particularly this invention relates to a method of preparing γ-esters of folic acid.

BACKGROUND AND SUMMARY OF THE INVENTION

A recent trend in cancer chemotherapy is the highly aggressive application of high-dose multiple drug treatment regimens at the earliest point of diagnosis. These protocols are limited by drug toxicity and severe physiological effects and patient fatalities are not uncommon. This situation has caused several members in the medical community to question whether the benefit/risk boundary has been exceeded with the agents currently available. Enhancement of the differential specificity of anticancer agents by selective targeting mechanisms might diminish such problems. The vitamin folic acid has attracted considerable attention as a potential means to selectively deliver covalently bound drug conjugates. Many human cancer cell lines have been found to have highly overexpressed membrane-associated folate receptor proteins which binds folic acid.

Previously, it has been shown that the natural receptor-mediated endocytosis pathway for the vitamin folic acid can be exploited to selectively and non-destructively deliver folate-conjugated small molecules, macromolecules, and drug carriers such as liposomes into cultured tumor cells. When folate is covalently linked to a folate molecule via its γ-carboxyl moiety, the affinity of the covalent conjugate for the folate cell surface receptor remains essentially unaltered. Further, following binding to the cell surface receptor, the conjugated folate is internalized by the cell in much the same manner as the unmodified vitamin. Recycling of the folate receptor can then lead to further accumulation of the folate conjugates in such target cells.

Unfortunately, a major impediment in design of folate conjugates centers around synthesis of such compounds. Current practice simply involves treatment of the substrate of choice with folic acid or a folic acid analog and a dehydrating agent, such as DCC. This results in a mixture of both the inactive α-conjugate and the active γ-conjugate often accompanied with the bis-functionalized derivative and/or recovered folic acid (see FIG. 1). Separation of these mixtures is often very difficult.

An alternative approach to the synthesis of differentially functionalized folic acid derivatives relies upon the acylation of monoesters of glutamic acid with pteroic acid. Unfortunately that strategy is compromised by the high cost of pteroic acid.

It is an object of the present invention to provide a method for regiospecific substitution of the γ-carboxylic acid functional group of folic acid and related compounds.

There is also provided in the present invention novel pteroic acid derivatives. The glutamic acid moiety of folic acid derivatives is cyclized to form a pyroglutamate group. The pyroglutamate group is nucleophilically displaced to yield pteroic acid derivatives.

This invention also encompasses a method directed to preparing pteroic acid hydrazides by reacting corresponding pyroglutamates with hydrazine.

Another aspect the present invention encompasses a method of preparing γ-substituted folic acid derivatives by reacting the corresponding pteroic azides with γ-substituted glutamate esters.

DETAILED DESCRIPTION OF THE INVENTION

In general terms, the present invention is directed toward a method of preparing γ-substituted folic acids and related compounds. The γ-substituted folic acid derivatives are key intermediates for preparing receptor binding γ-folate-drug conjugates. Current methodology for preparing folate conjugates result in formation of difficult to separate mixtures of the α-, γ- and bis-functionalized glutamate moiety of folic acid. The present invention provides intermediates and methods for the selective synthesis of folate-drug conjugates linked through the γ-carboxy group on the glutamic acid moiety of folic acid and related folate compounds.

One embodiment of the present invention is a compound of the formula

I wherein Q can be a OH or $NH_2$, Y is either hydrogen, nitroso, $C_1$–$C_4$ alkyl, $C_1$–$C_4$ alkanoyl, or a $C_1$–$C_4$ halosubstituted alkanoyl, including di- and tri-halosubstituted alkyl, and Z is either hydrazino or a pyroglutamate group, provided that when Z is pyroglutamate, Y is other than acetyl or trifluroacetyl.

The term $C_1$–$C_4$ alkyl includes a straight, branched or cyclic aliphatic chain having one to four carbon atoms. Typical $C_1$–$C_4$ alkyl groups include methyl, ethyl, propyl, isopropyl, butyl, iso-butyl, and tert-butyl.

The term $C_1$–$C_4$ alkanoyl includes ethanoyl, propanoyl, isopropanoyl, butanoyl, and t-butanoyl.

This invention is also directed to a method of preparing a compound of the formula

II wherein Q and Y are defined as above. The method comprises the step of reacting the corresponding pyrofolate (Formula I above, Z=pyroglutamate) with hydrazine, provided that when Y in the pyrofolate is trifluroacetyl, Y in the product hydrazide of Formula II is hydrogen.

In another embodiment, this invention is also directed to a method of preparing a γ-substituted compound of the formula

IV wherein Q is —OH or $NH_2$, and Y is hydrogen, or $C_1$–$C_4$ alkyl and R is alkyl. The method comprises the step of reacting a compound of the formula

V with an γ-alkyl glutamate in DMSO or DMF in the presence of a base.

Figure 2:
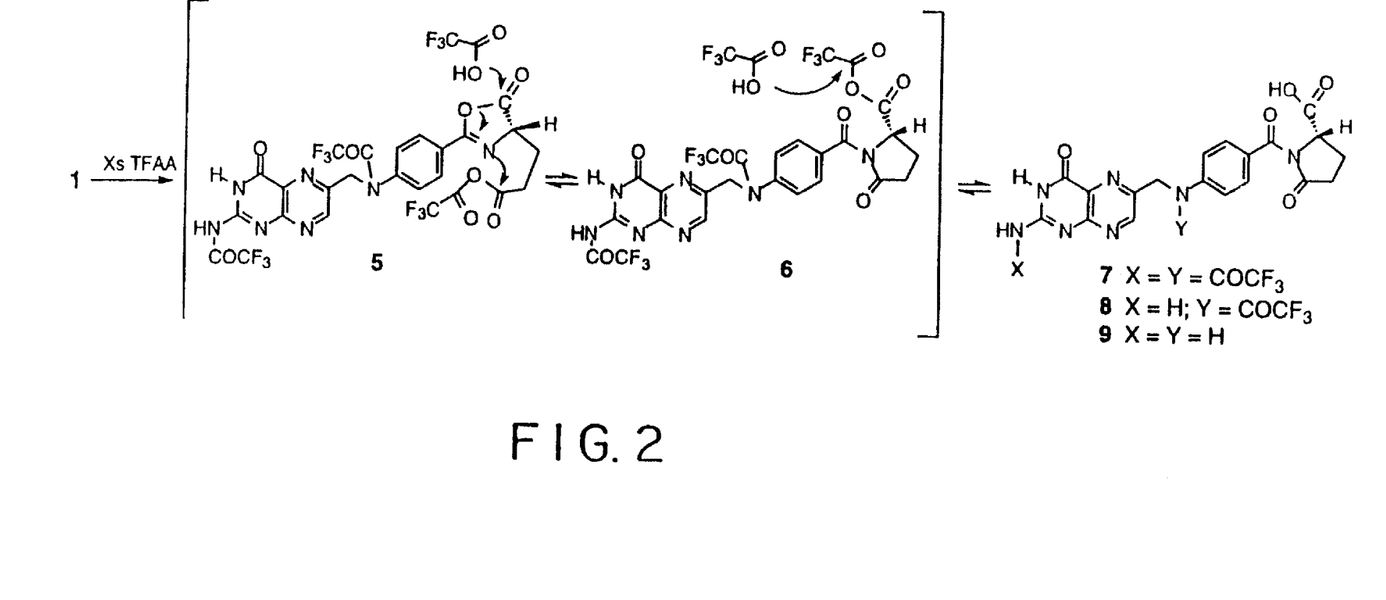
FIG. 2 depicts a reaction scheme for the formation of pyrofolate derivatives from folic acid in trifluoracetic anhydride.

Thus there is provided in accordance with this invention a method for preparation of γ-substituted folate derivatives. The initial step of this methodology involves the formation of a pyrofolate. The N10-trifluoroacetyl derivative of azlactone 8' (not the isomeric pyrofolate 8; see FIG. 2) has been alleged to result from reaction of folic acid 1 with trifluoroacetic anhydride (See FIG. 3). In addition, it has been reported that N10-acetyl aziactone Me-8' results from the analogous acetic anhydride reaction. (Temple, Jr., C.; Rose, J. D.; Montgomery, J. A. *J. Org. Chem.*, 46, 3666 (1981). Basic hydrolysis of Me-8' yields a mixture of folic acid 1 and pteroic acid 10, that is entirely consistent with the pyrofolate structure while an the unprecedented hydrolysis of the azlactone imine moiety had to be invoked to explain the production of pteroic acid. This structural misassignment has dire consequences vis-a-vis regiospecific functionalization of the two carboxylates of the glutamate moiety, since nucleophilic attack on the azlactone 8' would be expected to afford functionalization of the α-carboxyl moiety while activation of the carboxylic acid should enable regiospecific γ-functionalization. This is exactly the opposite regiochemistry that actually results from functionalization of the correct pyrofolate structure 8, and has resulted in further incorrect structural assignments.

Regiospecific functionalization of the γ-carboxylate of glutamic acid is routinely accomplished using urethane derivatives of pyroglutamic acid which exploit the γ-lactam moiety as an acylating agent. A search of the literature surprisingly revealed that pyrofolic acid 9 or its N-acylated derivatives are apparently unknown. Nevertheless, treatment of folic acid 1 with excess trifluoroacetic anhydride in THF for 10 h from 0° C. to 25° C. produces N2,10-bistrifluoroacetyl pyrofolic acid 7 as an extremely water-labile material which is believed to be a mixture of diacylated anhydride 6 and diacylated carboxylic acid 7 as judged by $^{19}$F-NMR of the crude reaction mixture. In any event, simply stirring the aforementioned material with neutral water affords N10-trifluoroacetyl pyrofolic acid 8 in a quantitative yield. (See FIG. 2). Compound 8 can be further transformed to pyrofolic acid 9 via deacylation with cesium carbonate and water (87%). Both compounds 8 and 9 are essentially racemic as determined using an enzymatic assay based upon carboxypeptidase G.

Figure 4:
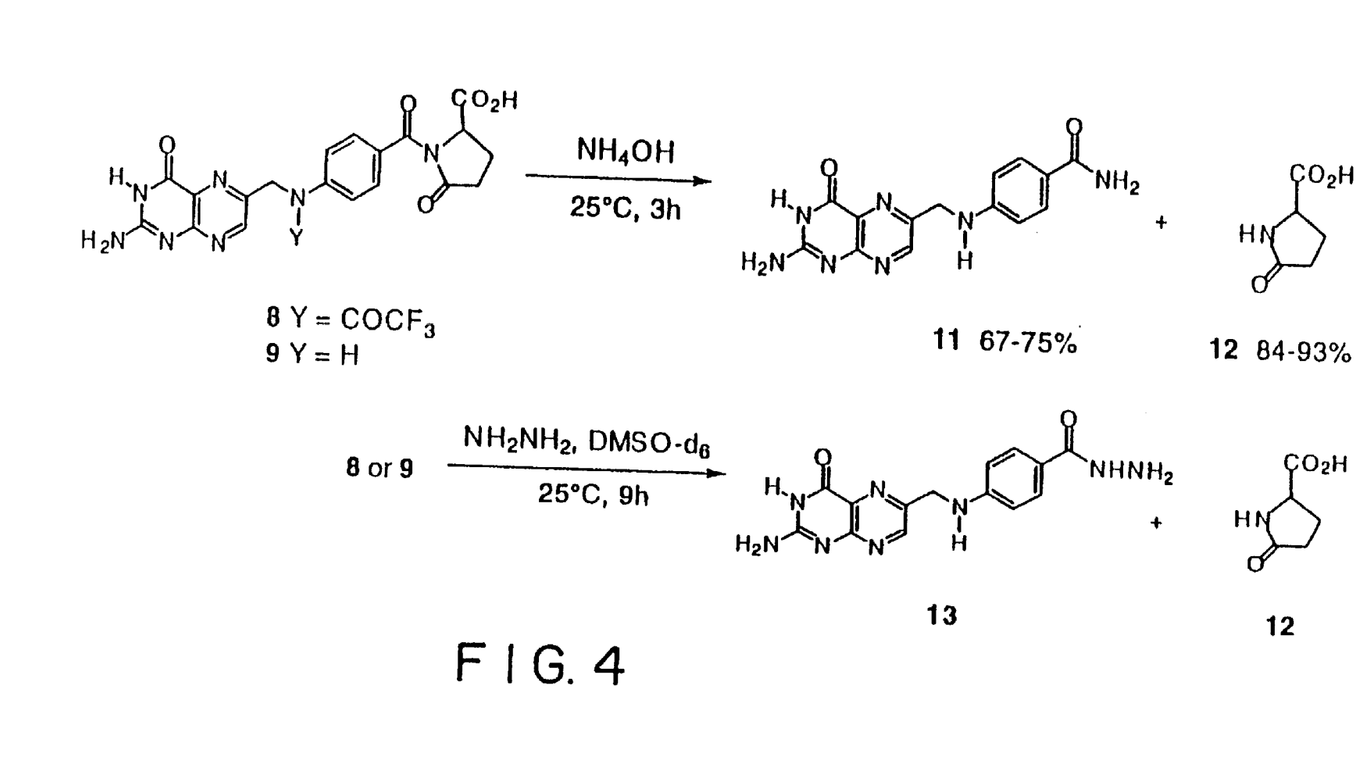
FIG. 4 illustrates the reaction of pyrofolate derivatives with ammonium hydroxide or hydrazine.

In order to provide a definitive structural assignment, both N10-trifluoroacetyl pyrofolic acid 8 and pyrofolic acid 9 were treated with excess concentrated ammonium hydroxide at 25° C. for several hours to afford pteroyl amide 11 along with pyroglutamic acid 12 in high yield (See FIG. 4), a finding which would be exceptionally difficult to rationalize with the alternative azlactone structures 8' and 9'. As expected, concomitant deacylation of the N10-trifluoroacetyl moiety occurred during the reaction. The isolated pyroglutamic acid 12 exhibited only ≦5% optical activity in accord with extensive racemization occurring during the synthesis of 8. Monitoring a pair of similar reactions of 8 and 9 with hydrazine (10 equiv.) in DMSO-$d_6$ at 25° C. for 9 h unambiguously produces a 1:1 mixture of pteroyl hydrazide 13 and pyroglutamic acid 12 in near-quantitative yield as assayed by $^1$H-NMR, and HPLC (FIG. 4 and Table 1, Entries 12, 13).

TABLE 1

Reactions of Nucleophiles with $N^{10}$-Trifluoroacetylpyrofolic acid 8 and pyrofolic acid 9

| Run | SM | Nucleophile and Conditions | Folic Acid Derivative 25 (yield[a] & Nuc=) | Pteroic Acid Derivative 26 (yield[a] & Nuc=) | Folate/Pteroate (25/26) Ratio[a] |
|---|---|---|---|---|---|
| 1 | 8 | $H_2O$, NaOH | 25a = 1 (52%, OH) | 26a = 10 (48%, OH) | 1.1 |
| 2 | 9 | $H_2O$, NaOH | 25a = 1 (68%, OH) | 26a = 10 (32, OH) | 2.1 |

TABLE 1-continued

Reactions of Nucleophiles with N¹⁰-Trifluoroacetylpyrofolic acid 8 and pyrofolic acid 9

| Run | SM | Nucleophile and Conditions | Folic Acid Derivative 25 (yield[a] & Nuc=) | Pteroic Acid Derivative 26 (yield[a] & Nuc=) | Folate/Pteroate (25/26) Ratio[a] |
|---|---|---|---|---|---|
| 3 | 8 | H₂O, HCl | 25b[b] (33%, OH) | 26b[b] (56%, OH) | 0.5 |
| 4 | 9 | MeOH, NaOMe | 25c (49%, OMe) | 26c (44%, OMe) | 1.1 |
| 5 | 9 | MeOH, LiOMe | 25c (81%, OMe) | 26c (19%, OMe) | 4.3 |
| 6 | 9 | MeOH, DBU | 25c (58%, OMe) | 26c (42%, OMe) | 1.4 |
| 7 | 8 | MeOH, TlOMe | 25c (35%, OMe) | 26c (58%, OMe) | 0.6 |
| 8 | 9 | MeOH, TlOMe | 25c (69%, OMe) | 26c (30%, OMe) | 2.3 |
| 9 | 9 | i-PrOH, TlOi-Pr | 25d (80%, O-iPr) | 26d (7%, O-iPr) | 11.5 |
| 10 | 9 | t-BuOH, TlOt-Bu | 25e (Nrc, Ot-Bu) | 26e (Nr[c], Ot-Bu) | NR[c] |
| 11 | 9 | DEG[d], NaH | 25f (48%, DEG'[e]) | 26f (22%[a], DEG'[e]) | 2.2 |
| 12 | 8 | NH₂NH₂, DMSO | 25g (0.9%, NHNH₂) | 26g = 13 (91%, NHNH₂) | 0.01 |
| 13 | 9 | NH₂NH₂, DMSO | 25g (9.1%, NHNH₂) | 26g = 13 (90%, NHNH₂) | 0.1 |
| 14 | 8 | NH₄OH, H₂O | 25h (33%, NH₂) | 26h = 11 (67%, NH₂) | 0.5 |
| 15 | 9 | NH₄OH, H₂O | 25h (60%, NH₂) | 26h - 11 (40%, NH₂) | 1.5 |
| 16 | 8 | PMBA[f] | 25I (0.9%, PMBA'[g]) | 26i (75%, PMBA'[g]) | 0.01 |

[a]Product ratio assayed by HPLC;
[b]This is the only instance in which the N¹⁰-trifluoroacetyl moiety survived the reaction conditions;
[c]NR = No reaction;
[d]DEG = HOCH₂CH₂OCH₂CH₂OH;
[e]DEG' = OCH₂CH₂OCH₂CH₂OH;
[f]PMBA - p-methoxybenzylamine;
[g]PMBA' - p-methoxybenzylamino.

Figure 5:
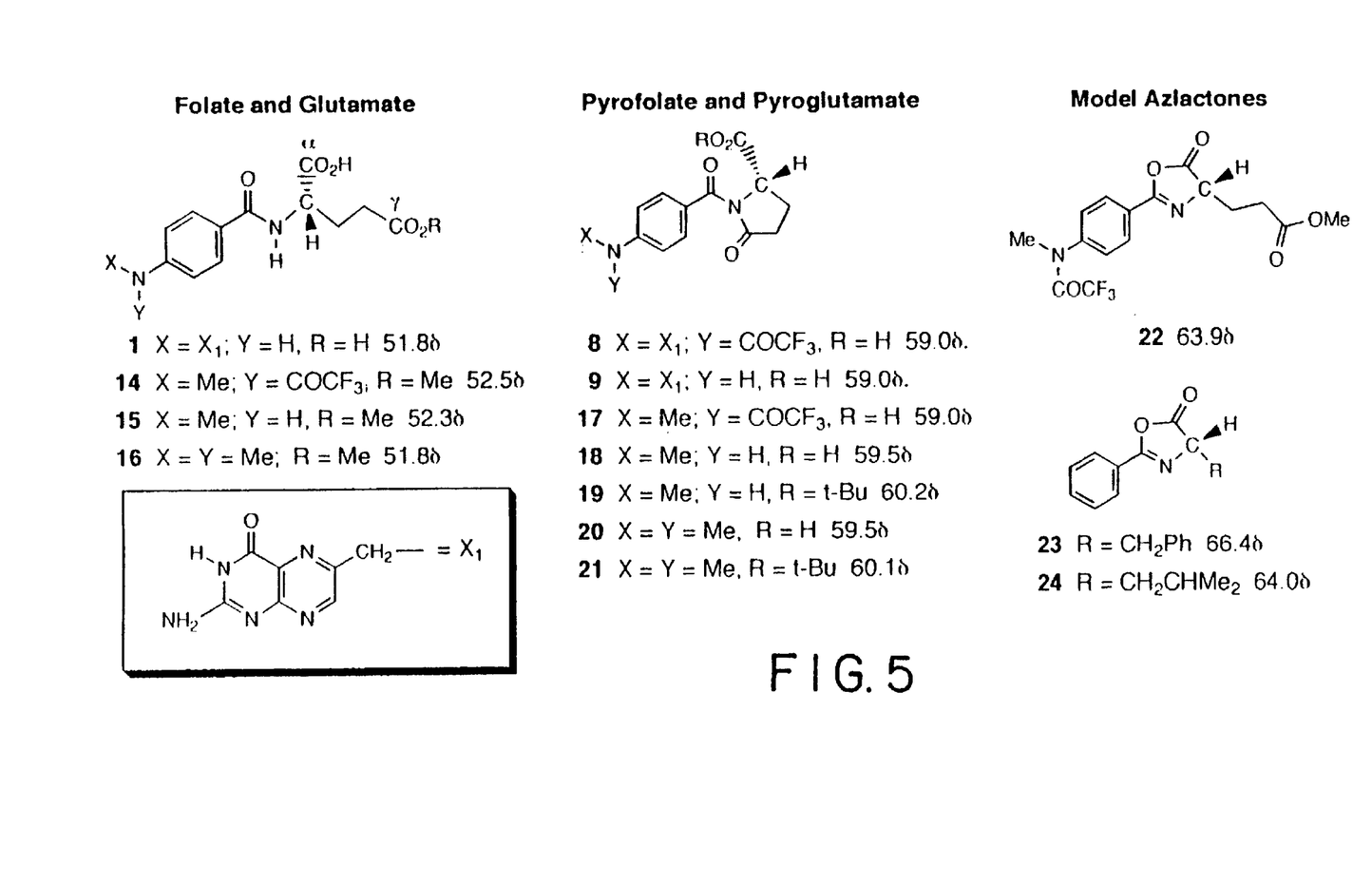
FIG. 5 illustrates a comparison of proton nuclear magnetic resonance signals for structurally related compounds.

Spectral evidence strongly supports the pyrofolate structure assigned to compounds 8 and 9. In particular, the $^{13}C$ NMR shift (DMSO-$d_6$) of the methine-bearing chiral carbon is highly diagnostic (FIG. 5). Folic acid 1 and the truncated p-aminobenzoyl glutamates 14–16, all resonate at ~52γ. Pyrofolates 8 and 9 and model p-aminobenzoyl pyroglutamates 17–21, exhibit their methine carbons between 59–60γ. This can be contrasted to model azlactones 22–24, which have chemical shifts around 64–66γ.

Figure 6:
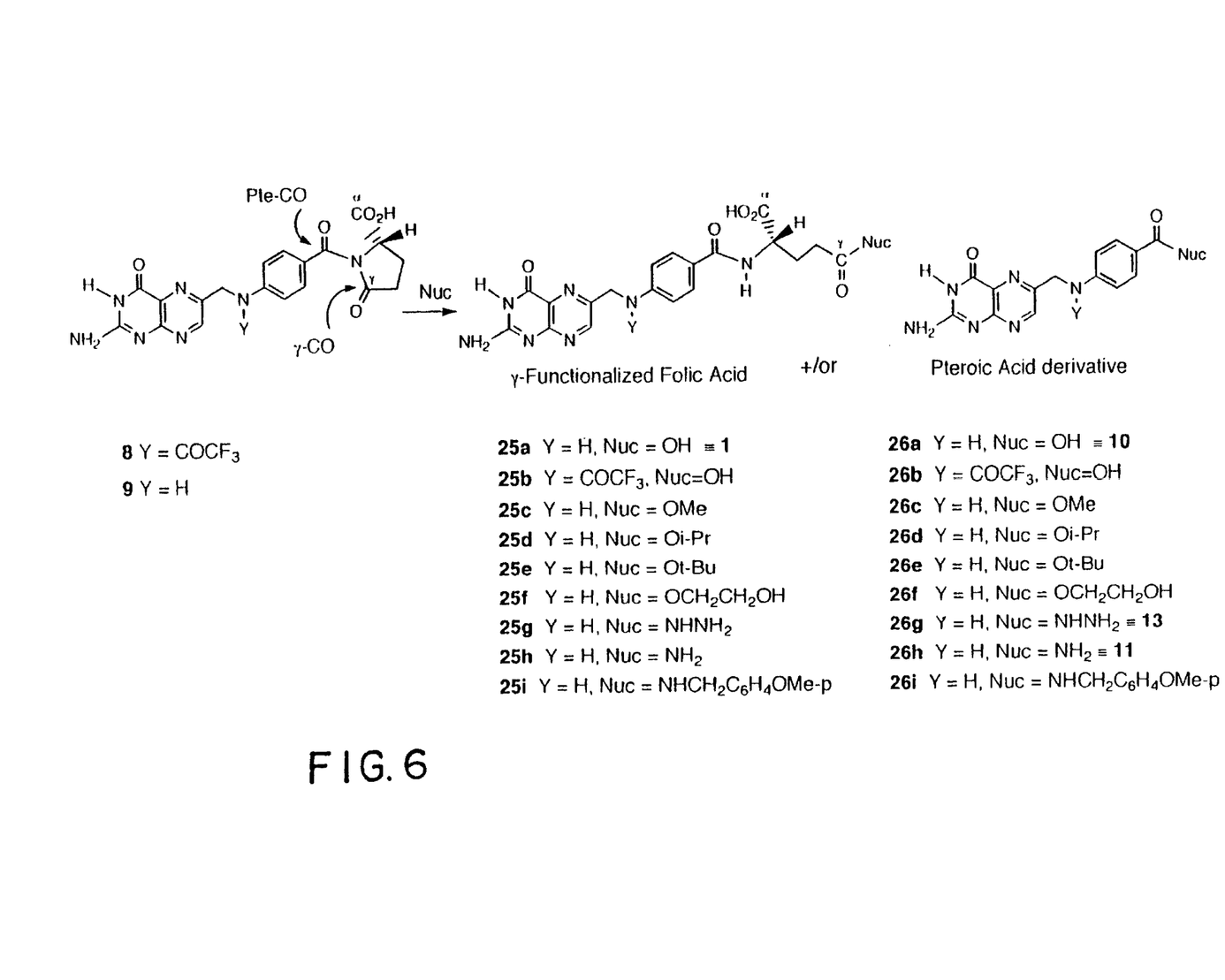
FIG. 6 illustrates alternate reaction pathways for the reaction of pyrofolate derivatives with nucleophiles (Nuc).

Having secured the pyrofolate structure of derivatives 8 and 9, the regiospecificity of the reaction of these substrates with oxygen and nitrogen nucleophiles was investigated. While the pyrofolate moiety insures complete regioselection between the α and γ-carbonyl groups of folic acid, the problem of differentiating between the two imide carbonyl groups (γ-CO and Pte-CO) of 8 and 9 remained to be determined. As can be seen in Table 1, Thallium[I]-mediated alcoholysis provides preferential generation of the folic acid derivatives 25c,d, the selectivity is an important function of the stearic environment of the alcohol. Aminolysis is currently unacceptable for direct drug conjugation, but as will be seen in FIG. 7, acyl hydrazide 26g, compound 13, is an ideal intermediate for the indirect synthesis of folates via nitrogen acylation of glutamates with pteroylazide 27. As expected, N10-trifluoroacetyl derivative 8 consistently exhibits a smaller folate/pteroate ratio (25/26) relative to compound 9 since increased nucleophilic attack at the benzoate carbonyl moiety is favored when the p-amino lone pair is unavailable for resonance deactivation. The full magnitude of this effect cannot be accurately assessed simply by inspection of Table 1, since there was no attempt to determine the rate of deacylation of the N10-trifluoroacetyl group relative to nucleophilic attack at the two competing carbonyl groups (See FIG. 6).

Figure 1:
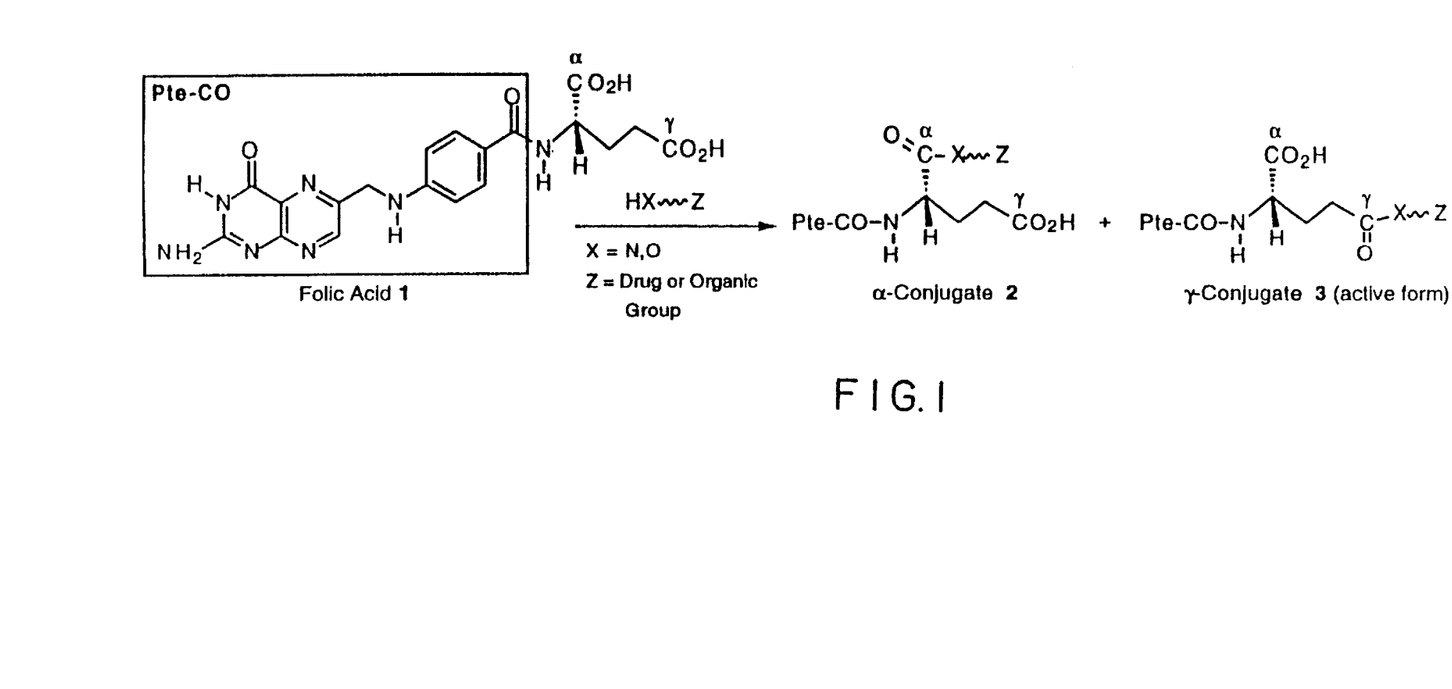
FIG. 1 depicts a reaction scheme as known in the art for forming folic acid conjugates.

Since it had already determined that pyrofolic acid derivatives 8 and 9 were essentially racemic, an indirect synthesis of the desired γ-functionalized folic acid derivative 3 shown in FIG. 1 was pursued via exploitation of the exceptionally selective (>99:1) reaction of hydrazine with compound 8 (Table 1, Entry 12). To this end, it was observed that conversion of pteroyl hydrazide 13 to pteroylazide 27 can be conveniently effected on reasonable (28 g) scale simply by treatment with 1.0 equivalent of t-butyl nitrite in trifluoroacetic acid containing 5 mol % potassium thiocyanate for 4 h at 10° C. HPLC analysis reveals that reactions run in the absence of potassium thiocyanate, an N-nitroso transfer catalyst, also produce 20–30% of N10-nitroso pteroylazide 28 along with pteroylazide 27. In the KSCN-free condition the remaining pteroyl hydrazide 13 slowly reacts with 28 to afford additional amounts of 27, but the reaction produces unacceptable levels of impurities relative to the optimized procedure.

Assay of pteroylazide 27 by UPLC reveals a purity of 91%. The known impurities include ~4% pteroic acid 10, ~2% of the aniline (PteNH₂) apparently resulting from Curtius rearrangement of 27, ~2% of pteroylamide (PteCO—NH₂ 11); and <1% of folic acid 1. Pteroylazide 27 may be further purified by dissolution/precipitation from trifluoroacetic acid/isopropanol, but the known impurities do not interfere, and the crude ~90% pure material can be used routinely for virtually all coupling operations. Unlike some acyl azides, pteroylazide 27 is quite stable; samples of the lemon-yellow solid may be stored in the dark in a freezer for at least 12 months without appreciable decomposition. Room temperature samples of 27 protected from light appear to have shelf lives of at least a month; while samples of 27 darken appreciably when exposed to light, their HPLC profiles are not substantially degraded.

Figure 7:
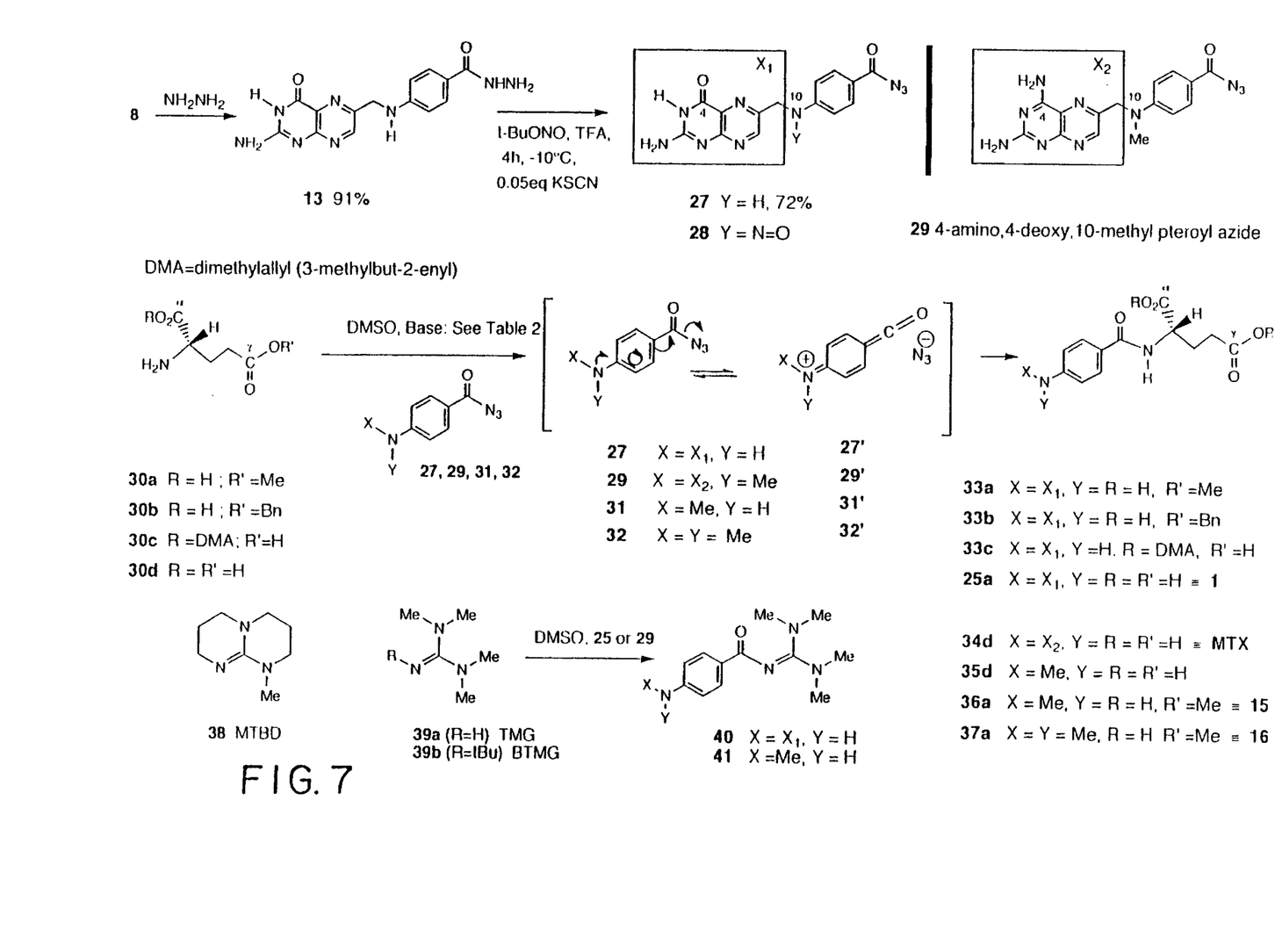
FIG. 7 illustrates a reaction scheme for the process of the present invention.

Therefore, pteroylazide 27 is now both easily available and serves as an excellent reagent for nitrogen acylation of differentially protected glutamates. As can be seen in Table 2, reaction of pteroylazide 27 in DMSO with L-glutamic acid 30d or glutamates 30a–c is strongly influenced by the nature of the added base, tetramethylguanidine 39a (TMG), t-butyltetramethylguanidine 39b (BTMG), and the expensive N-Methyl-1,5,9-Triazabicyclo[4.4.0]decene 38 (MTBD) all giving superb reactions. Our initial hypothesis is that the more basic nature of the guanidine bases, in concert with their ability to form soluble guanidinium carboxylates, is responsible for their ability to foster the acylation reaction. Surprisingly, it is noted that both Rosowsky and Chaykovsky (Rosowsky, A., et al., *J. Med. Chem.*, 24, 1450 (1981); Rosowsky, A., et al., *J. Med. Chem.*, 25, 960 (1982); Chaykovsky, M., et al., *J. Med. Chem.*, 18, 909 (1975); Chaykovsky, M., et al., *J. Med. Chem.*, 22, 869 (1979); Chaykovsky, M., et al., *J. Med. Chem.*, 22, 874 (1979)) have reported that the closely related acyl azide 29 is insufficiently reactive (in DMF or DMAC) to acylate glutamates or other α-aminoesters.

base followed by 1,6-elimination of the azide anion to generate the neutral p-quinoketene monoamine analog of 27′ (See FIG. 7: Y=lone pair; no charge on N). Presumably such a species would be an exceptionally reactive acylating agent. Two facts mitigate against this intriguing possibility: (1) The pKa of the N—H proton of 27 should be similar to p-methylamino methylbenzoate, having a pKa of 25.7 in DMSO, which is fairly distant from the pKa of H-TMG+ at 13.6 in water (est. ~20 in DMSO); consequently the concentration of the deprotonated form of 27 would be relatively small, but still attainable; (2) A second observation which argues against 27′ (FIG. 6: Y=lone pair, no charge on N) being a requisite intermediate is that azide 29 which bears no N—H proton, is a perfectly fine acylating agent, providing a high yield of synthetic L-methotrexate 34d upon reaction with L-glutamic acid 30d and tetramethylguanidine 39a, provided that DMSO or DMF is employed as the reaction solvent (Table 2, Entry 12). The fact that 29 reacts

TABLE 2

Acylation of glutamic Acid Derivatives 30-a-d in DMSO with Acyl Azides 27, 29, 31, 32

| Run | Acyl Azide & Glutamate | Base (# eq); DMSO pKa | Conditions | Product, and/or | HPLC conversion, (isolated yield) |
|---|---|---|---|---|---|
| 1 | 27 + L-30a | Et$_3$N (3 eq); 18.5 | 48h, 40° C. | L-33a | 23% |
| 2 | 27 + L-30a | Et$_3$N (5 eq); 18.5 | 48h, 40° C. | L-33a | 25% |
| 3 | 27 + L-30a | TMG (2 eq); 20 | 6h, 25° C. | L-33a | 100% (88%) |
| 4 | 27 + L-30a | MTBD (2 eq); 20 | 12h, 25° C. | L-33a | 100% |
| 5 | 27 + L-30a | BTMG (2 eq); 21 | 9h, 25° C. | L-33a | 100% |
| 6 | 27 + L-30a | DBU (2 eq); 19 | 8h, 25° C. | L-33a | 77% |
| 7 | 27 + L-30b | TMG (2 eq); 20 | 10h, 25 ° C. | L-33b | 100% (60%) |
| 8 | 27 + L-30c | TMG (2 eq); 20 | 12h, 25° C. | L-33c | 100% (82%) |
| 9 | 27 + L-30d | TMG (3 eq); 20 | 9h, 25° C. | L-25a = L-1 | 100% (67%) |
| 10 | 27 + L-30d | TMG (3 eq); 20 | 4h, 25° C. | D-25a = D-1 | 100% (40%) |
| 11 | 27 + D, L-30d | TMG (3 eq); 20 | 3h, 25° C. | D, L-25a = D, L-1 | 100% (38%) |
| 12 | 29 + L-30d | TMG (3 eq); 20 | 1h, 25° C. | L-34d | (100%) |
| 13 | 31 + L-30d | TMG (3 eq); 20 | 1h, 25° C. | L-35d | (73%) |
| 14 | 31 + L-30a | TMG (2 eq); 20 | 1h, 25° C. | L-36a - 15 | (67%) |
| 15 | 32 + L-30a | TMG (2 eq); 20 | 1h, 25° C. | L-37a = 16 | (72%) |

Examples of other bases suitable for use in accordance with this embodiment of the present invention include trimethylamine, triethylamine, tripropylamine, diisopropylamine, diisopropylethylamine, N-methylmorphine, tetramethyl piperidine, 1,5-diazabicyclo[4.3.0]non-5-ene (DBN), 1-8-diazabicyclo[5.4.0]undec-7-ene (DBU); dicyclohexylamine (DCHA), [1.8-bis(dimethylamino)naphthalene]dimethylethylamine; tetramethyl guanidine (TMG) t-butyl tetramethyl guanidine (BTMG), N-methyl, 1,5,9-triazobicyclo[4.4.0]undecene (MTBD), and 2,6-lutidine.

The dramatic reactivity difference between 27 and 29 appears to be a consequence of abstraction of the N—H proton of the p-aminobenzoyl azide moiety by the guanidine more rapidly with 30d than does 27 rules out the possibility that N—H deprotonation is an integral feature in these acylation reactions. Furthermore, there is no special reactivity conferred to these acyl azides by the pterion moiety, since p-monomethylaminobenzoyl azide 31 and p-dimethylaminobenzoylazide 32 both react with γ-methylglutamate 30a in DMSO or DMF in the presence of tetramethylguanidine to afford N-acyl glutamates 36a and 37a, respectively. The question as to whether these acylations are simply proceeding via the standard tetrahedral adduct or may progress via the intermediacy of p-quinoketene monoiminium ions 27′, 29′, 31′ and 32′ still remains to be determined (See FIG. 7).

Control studies show that in the absence of an added substrate, tetramethylguanidine (TMG) 39a slowly reacts with pteroylazide 27 or p-methylaminobenzoyl azide 31 to afford acylated guanidines 40 or 41 (See FIG. 7), but HPLC analyses of the reactions of 27 with glutamates 30a–d show only traces of compound 40. By comparison, HPLC analysis of a DMSO solution of 27 with pentaalkylguanidines BTMG 39b and MTBD 38 gives no evidence of guanidine acylation or any other reaction after 18 h at 25° C. This finding requires that, if formed, p-quinoketene monoiminium ion 27' must be in ready equilibrium with the starting acyl azide 27. DBU (est. pKa in DMSO ~19) 20c was found to be a less effective base in these reactions (Table 2, Entry 5), since a portion of the pteroylazide 27 was consumed via an unprofitable acylation-fragmentation sequence providing by-product 45 in 20% yield (see FIG. 8).

Since it had been previously observed that guanidine bases are capable of racemizing acylated glutamates (under more forcing conditions than were employed in the reactions listed in Table 2), the optical purity of the folic acid 1 (=25a) and several of its derivatives which had been produced was evaluated. For this purpose it was elected to employ the enzyme carboxypeptidase G, which has been shown to only deacylate the natural L-enantiomer of folic acid 1 to L-glutamic and pteroic acid 10, the yield of the latter material being determined by HPLC. In order to assay the pyrofolates 8 and 9 as well as the α- and γ-monoesters of folic acid L-33a and L-33c, an initial mild basic hydrolysis was required prior to the enzyme assay. As can be seen in Table 3, Entries 1,2, the synthetic folic acid L-1=25a was produced in enantiomerically pure form (within the limits of experimental error). Control reactions on synthetic D-1=25a and DL-1=25a (Table 3, Entries 3,4) serve to confirm the error limits of the enzymatic method at about ±2–3%.

Figure 8:
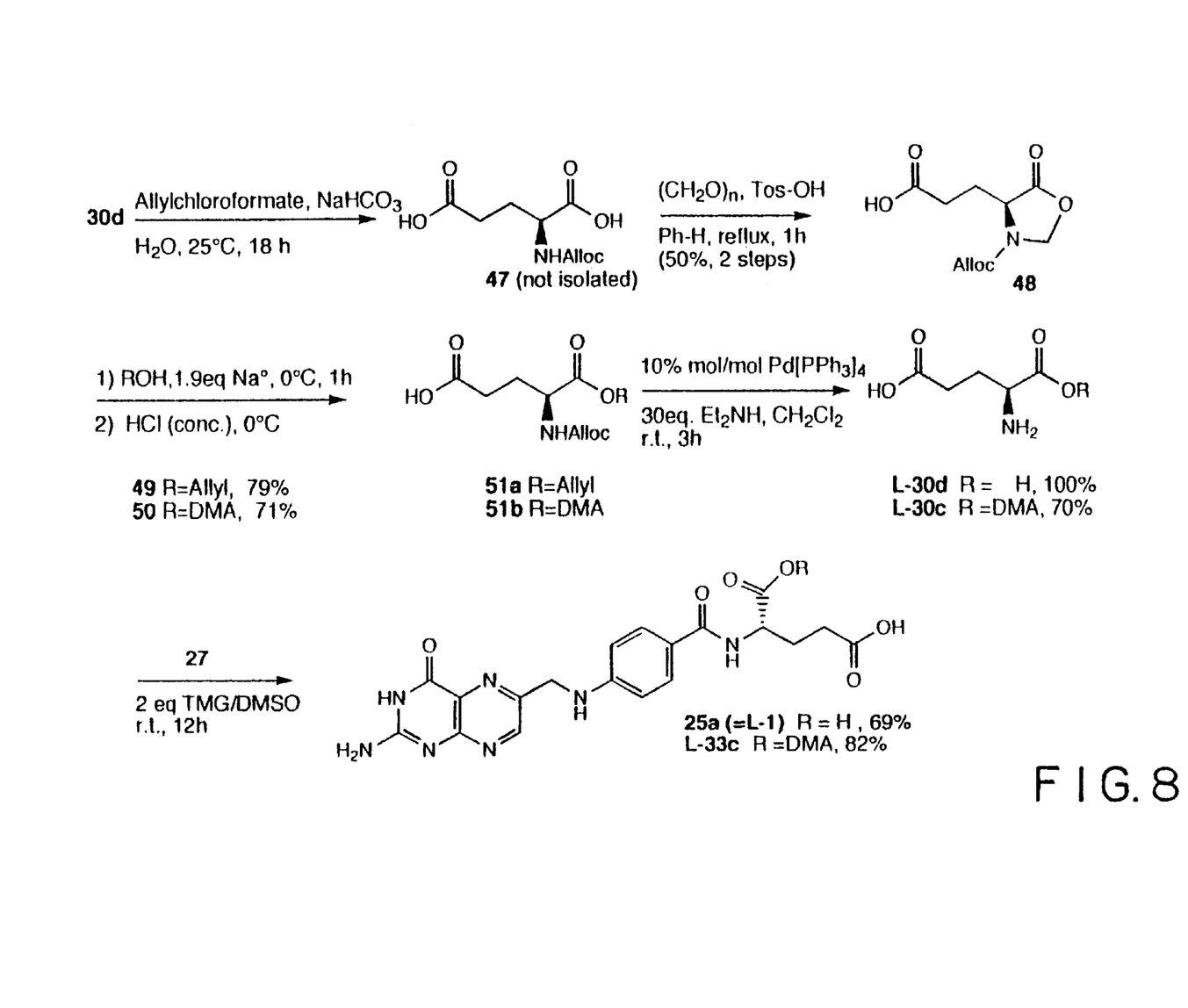
FIG. 8 illustrates the preparation of alpha glutamate esters.

Synthesis of bis alkylated glutamates 51a,b was initiated via reaction of L-glutamic acid 30d with allyl chloroformate to afford N-alloc-protected glutamic acid 47. This material was not purified but directly reacted with paraformaldehyde under the standard conditions 16 to provide N-alloc oxazolidinone 48 in 50% overall yield for the two steps. Reaction of this substrate with slightly less than 2 equivalents sodium metal in the presence of an excess of allyl 49 or dimethylallyl alcohol 50 provides α-alkylated and α-dimethylallylated N-alloc glutamates 51a,b, in 79% and 71% yield, respectively. Use of an excess of sodium results in partial racemization of glutamate 51b; in this instance 2.1 equivalents of sodium generated a product which was only 85.9% optically pure (Table 3, Entry 10a), while employment of the 1.9 equivalent conditions afforded material which was 96.7% optically pure as judged by the enzymatic assay (Table 3, Entry 10b). Since the synergistic value of Palladium [0]-mediated deprotection of the allyl and dimethylallyl protecting groups has been convincingly demonstrated for N-alloc esters. This superb strategy was used for cleavage of 51a,b. As can be seen in FIG. 8, reaction of 51a with diethylamine and 10 mol % Palladium tetrakistriphenylphosphine provides a quantitative yield of L-glutamic acid 30d, while similar reaction of dimethyl allyl ester 51b affords a 70% yield of α-DMA protected glutamate 30c. As indicated above, both these materials are shown to be essentially optically pure, as assayed after their conjugation (69–82%) with pteroyl azide 27, to afford 25a (=L-1) and L-33c, respectively (Table 3, Entries 3, & 10b).

Figure 9:
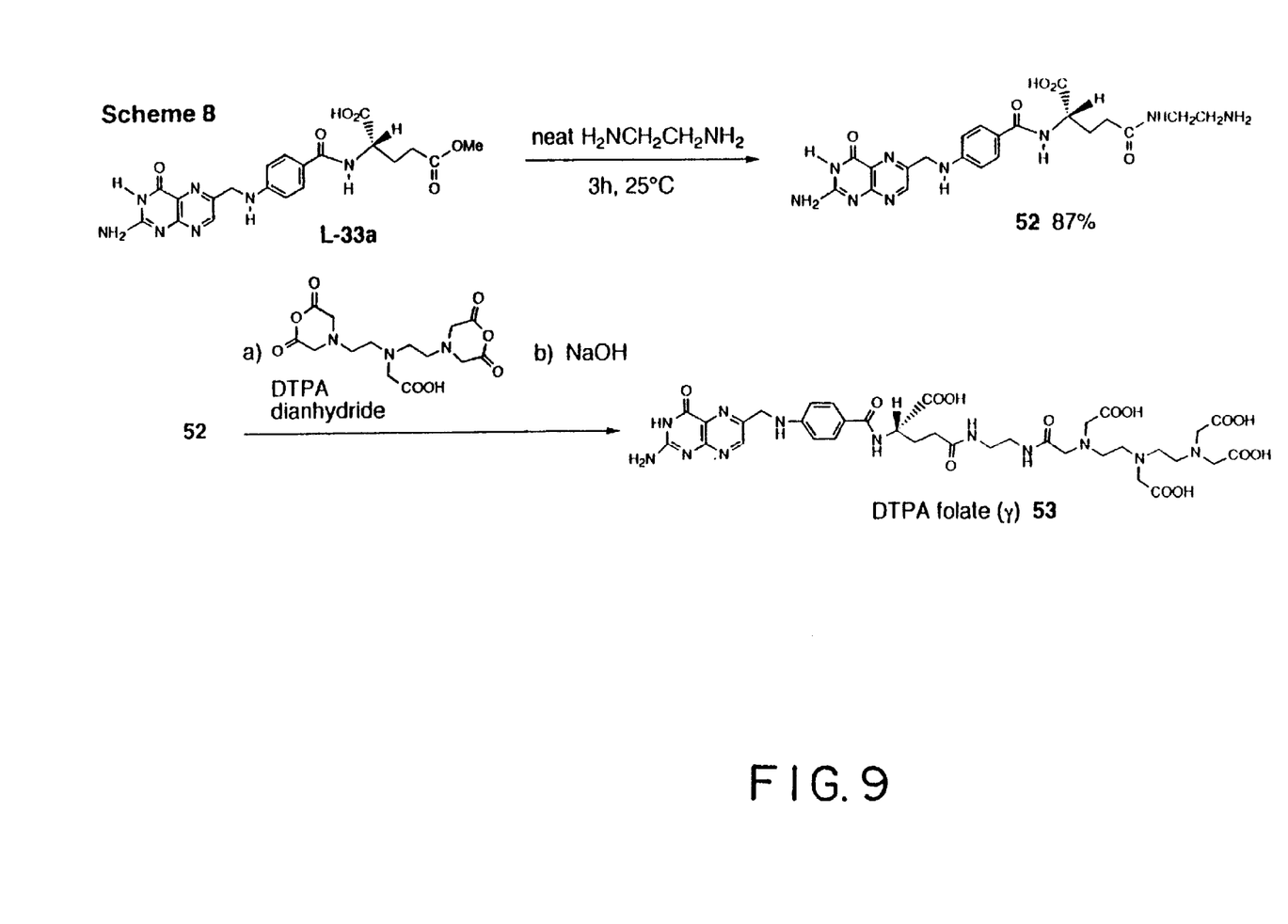
FIG. 9 illustrates a reaction scheme for use of γ-glutamate folate esters to prepare γ-substituted folic acid conjugates.

The value of pteroylazide 27 for the synthesis of folic acid analogs is exemplified in the preparation of DTPA-folate(γ) 53, a metal-binding ligand of an important new imaging agent with outstanding tumor specificity (see FIG. 9). The initial sample of 52, the precursor of 53, was prepared via the direct DCC/NHS coupling of ethylenediamine with folic acid 1 followed by separation of the various reaction components by extensive HPLC, the final yield of the requisite γ-conjugate 52 (FIG. 1 compound 3; X−Z= $NHCH_2CH_2NH_2$) being on the order of 10–15% on small scale. The current synthesis of 52, which is far superior in practical terms, now simply involves the reaction of synthetic γ-methylfolate L-33a (Table 2, Entry 3, 1.1 equiv) with neat ethylenediamine (50 equiv) for 3 h at 25° C. to afford 52 as a yellow solid in 87% yield, without the need of chromatography. Conversion of 52 to the tumor-specific metal-binding ligand DTPA-folate(γ) 53 has been previously described.

In conclusion, the first efficient syntheses of racemic N10-trifluoroacetyl pyrofolic acid 8, racemic pyrofolic acid 9, pteroylhydrazide 13, and pteroylazide 27 is provided. The latter reagent is an effective and economic reagent for the synthesis of differentially-functionalized folic acid derivatives. Application of this technology for the synthesis of new folate anticancer drug conjugates is under active investigation.

TABLE 3

Carboxypeptidase G anantiospecific hydrolysis of folic acid derivatives.

| Run | Compound (Source) | % Hydrolysis |
|---|---|---|
| 1 | L-1 (commercial[a]) | 96.7 |
| 2 | L-25a = L-1 (from Table 2) | 98.4 |
| 3 | L-25a = L-1 (from Table 3) | 98.6 |
| 4 | D-25a = D-1 (from Table 2) | 3.0 |
| 5 | D, L-25a = D, L-1 (from Table 2) | 52.3 |
| 6 | L-34d (NCI MTX[b]) | 96.1[c] |
| 7 | L-34d (MTX from Table 2) | 99.2[c] |
| 8 | DL-33a (from Table 1) | 54.4 |
| 9 | L-33a (from Table 2) | 96.8 |
| 10a | L-33c (from Table 2) | 85.9 |
| 10b | L-33c (from Table 2 & Scheme 7) | 96.7 |
| 11 | 8 (from Scheme 2) | 49.5 |
| 12 | 9 (from Scheme 2) | 51.7 |

[a]Commercial L-1 from Vitamins, Inc.; [b]A sample of L-methotrexate L-34d was provided by the National Cancer Institute; [c]D-34d is known not to be hydrolyzed by carboxypeptidase G.

EXPERIMENTAL SECTION

General Methods. Melting points were obtained on a MEL-TEMP apparatus and are uncorrected. Unless otherwise stated, reactions were carried out under argon in flame dried glassware. Tetrahydrofuran (THF) and diethyl ether ($Et_2O$) were distilled from sodium-benzophenone ketyl. Dichloromethane and benzene were distilled from calcium hydride. Cyclohexane was stored over sodium metal. Deuterated NMR solvents ($CDCl_3$ and $CD_3CN$) were stored over 4 Å molecular sieves for several days prior to use. Flash chromatography on silica gel was carried out (230–400 mesh silica gel was used), and reverse phase LC was used for preparative purpose (LiChroprep C-18, 310 mm×25 mm). $^1H$ and $^{13}C$ NMR spectra were obtained using GE QE-300 NMR and Varian Gemini 200 NMR spectrometers at 300 or 200 MHz and 75 or 50 MHz respectively. $^1H$ NMR chemical shifts are reported in ppm relative to the residual protonated solvent resonance: $CDCl_3$, γ 7.26; $C_6D_5H$, γ 7.15. Splitting patterns are designated as s, singlet; d, doublet, t, triplet; q, quartet; p, pentet; m, multiplet; br, broadened. Coupling constants (γ) are reported in Hz. $^{13}C$ NMR chemical shifts are reported in ppm relative to solvent resonance:, γ 77.00; $C_6D_6$, γ 128.00. Mass spectral data were obtained on a Finnigan 4000 mass spectrometer (low resolution) and a CEC 21 110 B high resolution mass spectrometer, with the molecular ion designated as M. All the chemicals were supplied by Aldrich Chemical Company, Inc, Milwaukee, Wis. 53233, or otherwise indicated.

EXAMPLE 1

Typical experimental procedure for coupling of pteroylazide 27 with glutamates:

To a stirred DMSO suspension of equal molar amounts of pteroylazide 27 (0.02~0.3M) and a glutamate (Table 2) was added two (three for glutamic acid) equivalents of tetramethylguanidine at room temperature. The mixture soon became homogeneous, and the reaction was normally complete within 12 h as indicated by analytical HPLC. The solution was filtered through a pad of celite to remove any traces of solid residue, and acetonitrile was slowly added to the stirred filtrate. The precipitated solid was filtered centrifuged to give the crude product after washing with diethyl ether and drying 18 h under vacuum. When appropriate, preparative LC was used to provide a purer sample. The procedure is exemplified below by the synthesis of folic acid L-1 and tetramethylguanidinium (L)-methyl folate (γ) 33a.

EXAMPLE 2

Synthetic Folic acid L-1 (=25a):

To a suspension of pteroylazide 27 (200 mg, 0.590 mmol) and L-glutamic acid (131 mg, 0.890 mmol) in DMSO (30 mL) was added neat tetramethylguanidine (0.222 mL, 1.77 mmol). The stirred mixture soon became homogeneous, and the reaction was complete after 9 h as indicated by analytical HPLC. The solution was filtered through a pad of celite to remove any traces of solid residue, and acetonitrile (50 ml) was slowly added to the stirred filtrate. The precipitated solid was then centrifuged to give the crude folic acid (248 mg) after washing with aqueous 1% HCl solution (10 mL×1), acetonitrile (10 mL×1), and diethyl ether (25 mL×2), and drying 18 h under vacuum. An analytical sample (174 mg, 67%) was obtained using preparative reverse phase HPLC. $^1$H NMR, UV, and analytical HPLC, all indicated the same as those of commercial folic acid. Decomp. point ~238° C. [α]25D=+17.4° (c=0.5 in 0.1N NaOH); 98.4% of L-folic acid by the enzyme assay. Analytical HPLC Rt=7.2 min (Flow rate: 0.7 mL/min; Eluent A: water and phosphate buffer 50 mmol/dm3, pH 7; Eluent B: acetonitrile; Gradient: 0 min, 2% B; 25 min, 50% B; Column: ECONOSPHERE C18, 150 mm×4.6 mm).

EXAMPLE 3

Determination of optical purity of folate derivatives listed in Table 3 using enzymatic hydrolysis with carboxypeptidase G:30:

The folic acid derivative (~2.5 mg) was dissolved in 1 mL Tris buffer containing 20 µg ZnCl2 and 50 microunit enzyme (Sigma Chemical Company) was added. The solution was incubated at 37° C. for 2 h. A 20 µL sample was tested by HPLC on a 4.6 m×250 mm MICROSORB C-18 reverse phase column (Eluent A: 5 mM phosphate buffer; Eluent B: acetonitrile; flow rate: 1 mL/min; gradient: 0–5 min, 5% B, 10–15, 25% B). Folic acid was eluted at 4.1 min, pteroic acid at 10.6 min, methotrexate at 10.8 min, and amino-N10-methyl pteroic acid at 11.9 min. Peak area was used as the standard for analysis.

For folate derivatives, ~5 mg was first dissolved in 1 mL 0.25 M NaOH and incubated at room temperature for 1 h. Then the solution was acidified by 1 M HCl until precipitation. After centrifugation, washing, and drying, the ~2.5 mg yellow pellet was dissolved in 1 mL Tris buffer and reacted with enzyme under the conditions described above.

EXAMPLE 4

N2,10-bis-Trifluoroacetylpyrofolic acid/anhydride 6/7:

To a mechanically stirred suspension of folic acid 1 (100 g, 0.23 mol, U.S.P. grade, supplied from Vitamins Inc., Chicago, Ill., 60601) and anhydrous tetrahydrofuran (1,000 mL) in a three-neck flask, trifluoroacetic anhydride (256 mL, 1.81 mol) was slowly added at 0° C. over ~0.5 h before warming the solution to 25° C. The mixture gradually turned into a dark brown homogeneous phase as the reaction proceeded. After 10 h, analytical HPLC showed that the reaction was complete by the appearance of a number of peaks (presumably a mixture of 7 and other trifluoroacetylated pyrofolic acids) and confirmed the absence of folic acid 1. The solution was filtered through a pad of celite to remove a small amount of solid residue. Using a rotary evaporator, the filtrate was concentrated to a dark brown viscous liquid (~300 mL), which was slowly transferred with an aid of tetrahydrofuran (~20 mL) to a flask of well-stirred benzene (1,500 mL). The precipitated yellowish solid was filtered and washed with diethyl ether (250 mL×1) to yield crude product 6/7 (151 g). $^1$H NMR (300 MHz, DMSO-d$_6$) γ 8.89 (s, 1H, C7-H), 7.65 (s, 4H, Ar), 5.25 (s, 2H, C9-H2), 4.71 (dd, J=4.2, 8.9 Hz, C19-H), 2.59~1.98 (overlap, 4H). $^{13}$C NMR (200 MHz, DMSO-d$_6$) γ 174.4, 172.6, 170.9, 169.1, 166.0, 165.3, 159.8, 159.1, 159.0, 158.3, 157.5, 156.4, 155.7, 155.1, 149.2, 147.4, 142.2, 135.1, 130.1, 129.4, 128.4, 124.9, 124.8, 119.2, 118.1, 113.5, 112.4, 107.7, 106.6, 58.7, 54.1, 31.4, 21.6. $^{19}$F NMR (300 MHz, DMSO-d$_6$) γ −65.66, −74.13, −80.47 (Integration ratio 1.0:0.93:0.13). Analytical HPLC Rt=12.7 min (Flow rate: 0.7 mL/min; Eluent A: water and phosphate buffer 50 mmol/dm3, pH 7; Eluent B: acetonitrile; Gradient: 0 min, 2% B; 25 min, 50% B; Column: ECONOSPHERE C18, 150 m×4.6 mm).

EXAMPLE 5

N10-Trifluoroacetylpyrofolic acid 8:

The crude N2,10-bis-trifluoroacetylpyrofolic acid/anhydride 6/7 (150 g) was dissolved in tetrahydrofiran (500 mL), followed by addition of ice (~100 g) with stirring. Analytical HPLC indicated that all the original peaks converged after ~3 h at 25° C. into a single one (N10-trifluoroacetylpyrofolic acid 8). The mixture was then slowly transferred to efficiently stirred diethyl ether (2,000 mL). The precipitated yellowish powder was filtered, triturated with diethyl ether, washed thoroughly with diethyl ether (200 mL×3), and dried 18 h under vacuum, giving 8 (123 g) in a quantitative yield from folic acid 1. $^1$H NMR (300 MHz, DMSO-d$_6$) γ 8.64 (s, H, C7-H), 7.62 (s, 4H, Ar), 5.12 (s, 2H, C9-H2), 4.70 (dd, J=3.2, 4.9 Hz, 1H, C 19-H), 2.54~2.43 (overlap, 4H). $^{13}$C NMR (300 MHz, DMSO-d$_6$) γ 176.8, 174.7, 172.9, 169.4, 161.2, 156.9, 156.4, 156.0, 155.8, 155.5, 154.5, 149.8, 149.7, 145.1, 142.5, 135.3, 130.3, 128.7, 118.5, 114.7, 110.9, 59.0, 54.4, 31.8, 21.9. $^{19}$F NMR (300 MHz, DMSO-d$_6$) γ −65.2. mass spectrum (FAB), 519 (MH+); HRMS calcd for $C_{21}H_{16}F_3N_7O_6$ 519.1114, found 519.1112. Softens and decomp. at 208~214° C. Elemental analysis calcd for $C_{21}H_{26}F_3N_7O_6 \cdot 0.5H_2O$ H 3.24, C 47.73, F 10.79, N 18.65; found H 3.04, C 47.63, F 10.72, N 18.64. [α]D25=+2.9,c=0.5 in DMSO (cf. commercial folic acid from Vitamins, Inc. =+14.4 at the same concentration). Analytical HPLC Rt=11.9 min (Flow rate: 0.7 mL/min; Eluent A: water and phosphate buffer 50 mmol/dm3, pH 7; Eluent B: acetonitrile; Gradient: 0 min, 2% B; 25 min, 50% B; Column: ECONOSPHERE C18, 150 m×4.6 mm).

EXAMPLE 6

Pyrofolic acid 9:

To a stirred homogeneous solution of N10-trifluoroacetylpyrofolic acid 8 (14 g, 27 mmol) and DMF (250 mL) was slowly added aqueous cesium carbonate (10 mL, 82 mmol) at 25° C. Analytical HPLC indicated completion of the reaction by disappearance of 8 in 5 h. The mixture was filtered through a pad of celite, and carefiilly acidified to pH 4 with 5% aqueous hydrochloric acid. The resulting precipitate was thoroughly washed with water (100 mL×3) by centrifigation, acetonitrile (100 mL×1), and diethyl ether (100 mL×2) by aspirator filtration. The yellowish product 9 (10.2 g, 89%) was obtained after drying 24 h at 60° C. under vacuum. $^1$H NMR (300 MHz, DMSO-$d_6$) γ 8.64 (s, H, C7-H), 7.41 (d, J=8.3 Hz, 2H, Ar), 6.58 (d, J=8.3 Hz, 2H, Ar), 4.70 (m, 1H, C19-H), 4.47 (d, J=4.7 Hz, 2H, C9-H2), 2.57~1.80 (overlap, 4H). $^{13}$C NMR (300 MHz, DMSO-$d_6$) γ 174.0, 172.8, 169.1, 161.2, 153.9, 152.2, 148.7, 148.4, 132.4, 132.3, 128.1, 120.4, 110.6, 59.0, 45.8, 31.6, 21.6. mass spectrum (FAB), 424 (MH+); HRMS calcd for $C_{19}H_{17}N_7O_5$ 424.1369, found 424.1365. Mp: decomp. at ~269° C. [α]D25=−1.2,c=0.5 in DMSO. Analytical HPLC Rt=9.0 min (Flow rate: 0.7 mL/min; Eluent A: water and phosphate buffer 50 mmol/dm3, pH 7. Eluent B: acetonitrile; Gradient: 0 min, 2% B; 25 min, 50% B; Column: ECONOSPHERE C18, 150 m×4.6 mm).

EXAMPLE 7

Pteroyl amide 11 and pyroglutamic acid 12:

N10-Trifluoroacetylpyrofolic acid 8 (540 mg, 1.04 mmol) was dissolved in aqueous concentrated ammonium hydroxide solution (25 mL). As the reaction proceeded, yellowish solid precipitated. After 14 h, the solid powder 11 (217 mg, 67%) was isolated by filtration, and washed with water (20 mL×3), methanol (20 mL×1), and ether (25 mL×2), and dried under vacuum. $^1$H NMR (300 MHz, DMSO-$d_6$) γ 8.63 (s, 1H, C7-H), 7.61 (d, J=8.3 Hz, 2H, Ar), 6.68 (d, J=8.3 Hz, 2H, Ar), 4.44 (d, J=5.2 Hz, 2H, C9-H2), $^{13}$C NMR (300 MHz, TFA/inserted DMSO-$d_6$ tube) γ 172.6, 158.6, 151.5, 149.6, 146.7, 145.9, 138.0, 132.6, 130.2, 125.8, 122.9, 53.2. mass spectrum (FAB), 311 (M+); HRMS calcd for $C_{14}H_{13}N_7O_2$ 312.1209 (MH+), found 312.1205. Decomp. point ~293° C. Analytical HPLC Rt=9.8 min (Flow rate: 0.7 mL/min; Eluent A: water and phosphate buffer 50 mmol/dm3, pH 7; Eluent B: acetonitrile; Gradient: 0 min, 2% B; 25 min, 50% B; Column: ECONOSPHERE C18, 150 mm×4.6 mm). To isolate pyroglutamic acid 12, the solvent of the above aqueous filtrate was removed by rotary aspirator, and the residue was then purified using preparative HPLC to give 12 (112 mg, 84%). $^1$H NMR was the same as the one of commercial pyroglutamic acid. [α]D25=−0.74 (c=1.84 in water). MP=154~158° C. Pyrofolic acid 9 (100 mg, 0.236 mmol) in a similar treatment with ammonium hydroxide yielded 11 (11 mg, 15%) and 12 (23 mg, 92%). 11's [α]D25=+0.09 (c=0.46 in water).

EXAMPLE 8

Pteroylhydrazide 13:

N10-trifluoroacetylpyrofolic acid 8 (49 g, 94 mmol) was dissolved in DMSO (1,000 mL) with mechanical stirring. To this homogeneous solution was added hydrazine (30 mL, 0.94 mol) while maintaining the temperature at 25° C. During the process, the flask was immersed in a water bath at 25° C. and the hydrazine was added slowly in order to moderate a gentle exotherm. The reaction was complete after 8 h as indicated by Analytical HPLC, and the mixture was filtered through a pad of celite to remove a trace of solid residue. To the filtrate was then slowly added methanol (1,000 mL) and the resulting precipitated solid was collected by aspirator filtration (or centrifugation), and washed thoroughly with methanol (200 mL×3) followed by diethyl ether (200 mL×2), to yield crude product 13 (28 g, 91%) after drying 18 h under vacuum. $^1$H NMR (300 MHz, $D_2$O/NaOD) γ 7.91 (s, H, C7-H), 6.98 (d, J=8.5 Hz, 2H, Ar), 6.47 (d, J=8.5 Hz, 2H, Ar), 4.04 (s, 2H, C9-H2). $^{13}$C NMR (300 MHz, DMSO-d6/HCl conc ~10/1 v/v.) γ 166.3, 158.6, 152.9, 152.8, 152.2, 148.1, 146.9, 130.1, 128.6, 117.9, 112.1, 46.0. mass spectrum (FAB), 327 (MH+); HRMS calcd for $C_{14}H_{14}N_8O_2$ 327.1318, found 327.1307. Decomp. point ~291° C. Analytical HPLC Rt=14.2 min (Flow rate: 0.7 mL/min; Eluent A: water and phosphate buffer 50 mmol/dm3, pH 7; Eluent B: acetonitrile; Isocratic, 5% B; Column: ECONOSPHERE C18, 150 mm×4.6 mm).

EXAMPLE 9

(DL)-methyl folate (γ) 25c (=33a):

To stirred suspension of pyrofolic acid 9 (1.1 g, 2.6 mmol) and methanol (150 mL) was added lithium hexamethyldisilazide (1.0M in THF, 7.8 mL, 7.8 mmol) at −10° C. The mixture soon became homogeneous, and the reaction was complete in 9 h at this temperature as indicated by analytical LC. The basic media was quenched with acetic acid (5 mL) at −78° C. The yellow precipitate was isolated by centrifigation, and then purified by preparative reverse phase HPLC to give the methyl folate 25c (804 mg, 70%). 1H NMR (300 MHz, DMSO-$d_6$) γ 8.60 (s, 1H, C7-H), 7.91 (d, J=7.3 Hz, 1H, N18-H), 7.58 (d, J=8.4 Hz, 2H, Ar), 7.25 (s, 2H, C2-NH2), 6.90 (t, J=5.3 Hz, 1H, N10-H), 6.60 (d, J=8.4 Hz, 2H, Ar), 4.45 (d, J=5.3 Hz, 2H, C9-H2), 4.22 (dd, J=7.6, 12.3 Hz, 1H, C19-H), 3.51 (s, 3H, OCH3), 2.47 (t, J=1.7 Hz, 2H, C21-H2), 2.36~1.88 (m, 2H, C20-H2). $^{13}$C NMR (300 MHz, DMSO-$d_6$) γ 174.9, 173.7, 166.7, 162.1, 156.6, 154.8, 151.2, 149.0, 148.9, 129.4, 128.3, 122.0, 111.8, 52.9, 51.8, 46.4, 30.7,27.3. LRMS (PDMS) (MH+) 455, found 455.5. Decomp. point ~251° C. Analytical HPLC Rt=10.4 min (Flow rate: 0.7 mL/min; Eluent A: water and phosphate buffer 50 mmol/dm3, pH 7; Eluent B: acetonitrile. Gradient: 0 min, 2% B; 25 min, 50% B; Column: ECONOSPHERE C18, 150 mm×4.6 mm).

EXAMPLE 10

Pteroylazide 27 (and N10-Nitroso Pteroylazide 28):

To a stirred suspension of pteroylhydrazide 13 (28 g, 86 mmol) and potassium thiocyanate (0.41 g, 4.2 mmol) was added ice-cold trifluoroacetic acid (220 mL). After the solid dissolved, the reaction mixture was cooled to −10° C., followed by slow addition of neat tert-butyl nitrite (10 mL, 86 mmol). Monitoring by analytical HPLC indicated that the reaction was complete in 4 h after which time the reaction was warmed to 25° C. In addition to the desired pteroylazide 27, Analytical HPLC sometimes showed generation of a small amount (~10%, due to 90% purity of pteroylazide 27) of N10-nitrosopteroylazide 28, which could be instantly converted into pteroylazide 27 at 25° C. simply by addition of sodium azide (0.5 equiv. per equiv. of 13 used in the reaction) to the reaction mixture. The solution was then filtered through a pad of celite to remove a trace of solid residue. Slow addition of isopropanol (250 mL) to the stirred filtrate led to an orange powder, which was collected by centrifugation, washed thoroughly with water (500 mL×3), acetonitrile (500 mL×1), diethyl ether (200 mL×2), and finally dried 24 h under vacuum. Multiple cycles of the precipitation process were used in the trifluoroacetic-acid-isopropanol combination to obtain material of even higher purity (known impurities include ~4% pteroic acid 10, 2% of the aniline apparently resulting from Curtius rearrangement of pteroylazide 27, ~2% of pteroylamide 11, and <1% folic acid.). Normally, a purity of more than 90% (determined by HPLC) was achieved after a single purification cycle. The pteroylazide 27 (21 g, 72%) thus obtained was stored at −15° C. with protection from light. 27: $^1$H NMR (300 MHz, DMSO-$d_6$) γ 8.63 (s, 1H, C7-H), 7.65 (d, J=8.7 Hz, 2H, Ar), 7.57 (m, 1H, N10-H), 6.67 (d, J=8.7 Hz, 2H, Ar), 4.49 (d, J=5.8 Hz, 2H, C9-H2). $^{13}$C NMR (300 MHz, DMSO-$d_6$) γ 171.0, 158.6, 153.9, 152.7, 152.5, 148.3, 146.8, 131.8, 128.3, 117.6, 112.2, 45.8. mass spectrum (FAB), 338 (MH+); HRMS calcd for $C_{14}H_{11}N_9O_2$ 338.1114, found 338.1110. Decomp. point ~180° C. Analytical HPLC Rt=18.0 min (Flow rate: 0.7 mL/min; Eluent A: water and phosphate buffer 50 mmol/dm3, pH 7; Eluent B: acetonitrile; Gradient: 0 min, 2% B; 25 min, 50% B; Column: ECONOSPHERE C18, 150 mm×4.6 mm). 28 $^1$H: NMR (300 MHz, DMSO-$d_6$) γ 8.74 (s, 1H, C7-H), 8.08 (d, J=8.6 Hz, 2H, Ar), 7.91 (d, J=8.6 Hz, 2H, Ar), 5.52 (s, 2H, C9-H2). $^{13}$C NMR (300 MHz, DMSO-$d_6$) γ 171.6, 160.3, 153.8, 153.3, 149.3, 146.7, 145.1, 131.1, 129.0, 128.5, 120.0, 46.9. Analytical HPLC Rt=19.2 min (Flow rate: 0.7 mL/min; Eluent A: water and phosphate buffer 50 mmol/dm3, pH 7; Eluent B: acetonitrile; Gradient: 0 min, 2% B; 25 min, 50% B; Column: ECONOSPHERE C18, 150 mm×4.6 mm).

EXAMPLE 11

4-[[(2,4-Diamino-6pteridinyl)methyl]methylamino]benzoyl azide 29:

A solution of 56 (100 mg, 0.31 mmol), diphenyllphosphoryl azide (0.13 mL 0.46 mmol), and $Et_3N$ (0.09 mL, 0.62 mmol) in DMSO (5 mL) was stirred for 20 h. THF (10 mL) was then added and the precipitate was filtered to give 29 (92 mg, 83%). $^1$HNMR is the same as that reported in the literature.

EXAMPLE 12

Tetramethylguanidinium (L)-methyl folate (γ) 33a (R=TMG-H+):

To a suspension of pteroylazide 27 (5 g, 14.8 mmol) and methyl glutamate (γ) (2.63 g, 16.3 mmol) in DMSO (50 mL) was added neat tetramethylguanidine (3.7 mL, 29.7 mmol). The stirred mixture soon became homogeneous, and the reaction was complete after 6 h as indicated by analytical HPLC. The solution was filtered through a pad of celite to remove a trace of solid residue, and acetone (400 ml) was slowly added to the stirred filtrate. The precipitated solid was then filtered to give the crude tetramethylguanidinium salt of methyl folate (γ) 33a (R=TMG-H+): (6.1 g, 88%) after washing with diethyl ether (50 mL×2), and drying 18 h under vacuum. $^1$H NMR (300 MHz, DMSO-$d_6$) γ 8.58 (s, 1H, C7-H), 7.55 (d, J=8.4 Hz, 2H, Ar), 6.87 (t, J=5.3 Hz, 1H, N10-H), 6.62 (d, J=8.4 Hz, 2H, Ar), 4.41 (d, J=5.3 Hz, 2H, C9-H2), 3.98 (dd, J=7.6, 12.3 Hz, 1H, C19-H), 3.49 (s, 3H, OCH3), 2.81 (s, 12H, teramethylguanidine), 2.40~2.18 (m, 2H, C21-H2), 2.17~1.78 (m, 2H, C20-H2). mass spectrum (FAB), 454 (M−H+); HRMS calcd for $C_{20}H_{21}N_7O_6$ 454.1475, found 454.1445. Spiking experiments in $^1$H NMR and analytical HPLC showed this material to be identical to 25c except for the added presence of TMG.

EXAMPLE 13

N-alloc-glutamic acid 47:

To 50 g (340 mmol), of L-glutamic acid in 340 mL of distilled water was added 72 g (857 mmol) of sodium bicarbonate in several portions. After the bubbling ceased, 56 mL (510 mmol) of allylchloroformate was added all at once and the solution left to stir for 18 hours at 25° C. The pH was adjusted to 1 using concentrated hydrochloric acid and assayed using pH paper. The solution was transferred to a separatory funnel and extracted 10 times with ethyl acetate. The combined organics were rinsed with brine and dried over magnesium sulfate. The solvent was removed in vacuo to give 57 g (73%) of crude 47 as a colorless syrup.

EXAMPLE 14

3-(3-allyloxycarbonyl-5-oxo-1,3-oxazolan-4-yl)propanoic acid 48:

56.9 g (246 mmol) of 47, 16 g (492 mmol) of paraformaldehyde, 4.7 g (24.6 mmol) of p-toluene sulfonic acid and 1.2L of benzene were combined in a round-bottom flask equipped with a stir bar and a Dean-Stark trap and heated at reflux for 1 hour. The solvent was removed in vacuo, and the residue was purified by column chromatography ($SiO_2$ 4:1 hexane/ethyl acetate) to afford 48 (40.6 g, 68%) as a white solid. $^1$HNMR (300 MHz, $CDC_{l3}$) γ 5.90 (m, 1H), 5.55 (m, 1H), 5.30 (m, 1H), 4.66 (d, 5.85 Hz, 2H), 4.41 (t, 6.01 Hz, 1H), 2.54 (t, 6.95 Hz, 2H), 2.28 (m, 2H). $^{13}$CNMR (75 MHz, $CDC_{l3}$), γ 177.4, 171.6, 152.9, 131.4, 118.7, 77.6, 66.8, 53.7, 28.9, 25.4. mass spectrum (CI), 244 (M+H+, base peak); HRMS calcd for $C_{10}H_{13}NO_6$ 244.0821, found 244.0823.

EXAMPLE 15

N-alloc, α-allylglutamate 51a:

0.43 g (18.7 mmol) of elemental sodium was added in small pieces to 197 mL of allyl alcohol cooled to 0° C. under argon in a flame-dried round bottom flask. After all the sodium had dissolved, 2.39 g (9.83 mmol) of oxazolidinone 48 in 20 mL of allyl alcohol was cannulated into the solution of alkoxide. After stirring for 1 hour at 0° C., the pH was adjusted to 1 using concentrated hydrochloric acid and pH paper. The solution was transferred to a separatory finnel and diluted with and equal volume of water and extracted 6 times with ethyl acetate. The combined organics were rinsed with brine and dried over magnesium sulfate. The solvent was removed in vacuo, and the residue was purified by column chromatography ($SiO_2$, 4:1 hexane/ethyl acetate) to afford 51a (2.1 g, 79%) as a pale yellow oil. $^1$HNMR (300 MHz, $CDC_{l3}$) γ 5.85 (m, 2H), 5.43 (d, 7.98 Hz, N—H), 5.26 (m, 4H), 4.64 (d, 5.75 Hz, 2H), 4.57 (d, 5.33 Hz, 2H), 4.42 (m, 1H), 2.48 (m, 2H), 2.24 (m, 1H), 2.0 (m, 1H). $^{13}$CNMR (75 MHz, $CDC_{l3}$), γ 176.8, 171.4, 155.8, 132.1, 131.0, 118.2, 117.2, 65.5, 65.4, 52.8, 29.4, 26.4. mass spectrum (CI), 272 (M+H+, base peak); HRMS calcd for $C_{12}H_{17}NO_6$ 272.1134, found 272.1142.

EXAMPLE 16

N-alloc, α-dimethylallylglutamate 51b:

0.54 g (23.5 mmol) of elemental sodium was added in small pieces to 250 mL of allyl alcohol cooled to 0° C. under argon in a flame-dried round-bottom flask. After all the sodium had dissolved, 3.0 g (12.3 mmol) of 48 in 25 mL of allyl alcohol was cannulated into the solution of alkoxide. After stirring for 1 hour at 0° C., the pH was adjusted to 1 using concentrated hydrochloric acid as monitored using pH paper. The solution was transferred to a separatory funnel and diluted with and equal volume of water and extracted 6 times with ethyl acetate. The combined organics were rinsed with brine and dried over magnesium sulfate. The solvent was removed in vacuo, and the remaining liquid distilled under vacuum to remove the excess dimethylallyl alcohol (0.10 mm Hg, b.p. 39° C.). The residue was purified by column chromatography ($SiO_2$, 4:1 hexane/ethyl acetate) to afford 51b (2.6 g, 71%) as a pale yellow oil. $^1$HNMR (300 MHz, $CDCl_3$) γ 5.90 (m, 1H), 5.42 (d, 8.0 Hz, N—H), 5.30 (m, 3H), 4.64 (d, 7.31 Hz, 2H), 4.57 (d, 5.56 Hz, 2H), 4.40 (m, 1H), 2.47 (m, 2H), 2.22 (m, 1H), 1.98 (m, 1H), 1.76, (s, 3H), 1.71 (s, 3H). $^{13}$CNMR (75 MHz, CDCl$_3$), γ 177.0, 171.8, 155.8, 139.5, 132.2, 117.6, 117.4, 65.5, 62.1, 52.9, 29.6, 27.0, 25.3, 17.6. mass spectrum (CI), 300 (M+H+, base peak); HRMS calcd for C$_{14}$H$_{21}$NO$_6$ 300.1447, found 300.1459.

EXAMPLE 17

2-Aminoethyl folic acid, γ-amide 52 [EDTA-folate (γ)]:

To the crude tetramethylguanidinium (L)-methyl folate (γ) 33a (R=TMG-H+) (2.8 g, 5.95 mmol) was added ethylenediamine (20 mL, 0.3 mol) with stirring at 25° C. The solid gradually dissolved as it reacted with the diamine. The reaction was complete in 3 h as indicated by analytical HPLC, and filtration gave a clear solution which was then transferred to a well-stirred mixture of acetonitrile and diethyl ether (1:1 v/v, 500 mL). The precipitated solid was collected by centrifugation, re-dissolved in water (500 mL), followed by addition of aqueous 5% hydrochloric acid until pH=7.0, which effected precipitation of the product. Centrifigation was used to collect the precipitate, which was triturated with water, and washed thoroughly with water (250 mL×3) to remove any trace of ethylenediamine ($^{1}$HNMR was used to assay for the presence of the diamine.). A yellow solid (2.1 g, 88%) was obtained after washing with acetonitrile (100 mL×1), diethyl ether (50 mL×3), and drying 24 h under vacuum. 52: $^1$H NMR (300 MHz, DMSO-d$_6$/CF$_3$CO$_2$D~10/1 v/v) γ 8.75 (s, 1H, C7-H), 7.66 (d, J=8.6 Hz, 2H, Ar), 6.63 (d, J=8.6 Hz, 2H, Ar), 4.57 (s, 2H, C9-H2), 4.34 (dd, J=4.0, 9.6 Hz, 1H, C19-H), 3.28~3.13 (m, 2H, C24-H2), 2.80 (m, 2H, C25-H2), 2.16(m, 2H, C21-H2), 2.15~1.85 (m, 2H, C20-H2). $^{13}$C NMR (300 MHz, D$_2$O/NaOD) γ 178.8, 176.0, 173.1, 169.5, 164.0, 155.5, 151.1, 147.3, 147.2, 129.0, 128.2, 121.4, 112.5, 55.3, 45.8, 42.0, 39.8, 32.8, 28.0. mass spectrum (FAB), 484 (MH+); HRMS calcd for C$_{21}$H$_{25}$N$_9$O$_5$ 484.2057, found 484.2062. [α]D25=+4.5,c=0.4 in 1.0N NaOH. Decomp. point ~278° C. Analytical HPLC Rt=15.4 min (Flow rate: 0.7 mL/min. Eluent A: water and phosphate buffer 5 mmol/dm3, pH 7; Eluent B: acetonitrile; Gradient: 0 min, 1% B. 15 min, 10% B. Column: ECONOSPHERE C18, 150 mm×4.6 mm).

EXAMPLE 18

4-[[(2,4-Diamino-6-pteridinyl)methyl]methylamino] benzoic acid 56:

The sodium salt of 34d (equivalent to 200 mg, 0.44 mmol, from the National Cancer Institute) was dissolved in 5 mL of 0.1M Tris buffer. Carboxypeptidase G ~5 units) and ZnCl$_2$ (1 mg) were added and the pH of the solution was adjusted to 7.2 with concentrated HCl. The solution was shaken in a incubator at 38° C. for 2 days, and the mixture (pH 8.4) was then adjusted to pH 3.5 with dilute HCl. The precipitated yellow solid was filtered; washed with H$_2$O, EtOH, and Et$_2$O and dried to give the known acid 56 (152 mg, 96%). $^1$HNMR is the same as that reported in C. J. Pouchert Ed., The Aldrich Library of NMR Spectron 2nd ed. Aldrich Chemical Co. (1983).

EXAMPLE 19

Production of DTPA-Folate:

Dissolve 1.0 g EDA-folate(γ) (2.1 mmol) in 50 ml DMSO by bath sonication overnight. Then the dark yellow solution was slowly added to a stirring suspension of 20 g DTPA dianhydride (5.6 mmol) in 10 mL anhydrous DMSO. The mixture became homogeneous by the end of addition. Analytical HPLC showed the absence of the starting material EDA-folate after 30 min. at which time the reaction mixture was filtered through a pad of celite to remove traces of solid residue. After reducing the temperature of the reaction mixture with ice bath, 10 mL 2.4 N NaOH was added to quench the reaction and to neutralize the solution. The resulting precipitate containing the majority of the DTPA-folate(γ) produced was separated by centrifugation from the supernatant. The yellow pellet was then washed with 100 mL acetonitrile, dissolved in 50 mL water, and the pH of the solution was adjusted to 7 with concentrated HCL. After filtration to remove the solid residue, the clear orange solution was directly purified on a LiChroprep C-189 reversed phase MPLC column (310 mm×25 mm, 45–60 μm) using 10 mM ammonium bicarbonate buffer as the eluant (t$_r$=20–35 min, flow rate: 1 mL/min). The collected product was concentrated by vacuum and further purified by preparative HPLC on the Microsorb C-18 column with a gradient (eluant A: 10 mM ammonium bicarbonate buffer, pH 7.4; eluant B: acetonitrile; gradient: 0 min, 4$ B; 10 min, 12% B; 15 min, 15% B; flow rate: 10 mL/min; t$_r$–6.3 min) to remove residual bis-conjugated side product and to achieve 0.85 g DTPA-folate after lyophilization with a purity above 99% and a yield of 47%. Analytical HPLC on the Econosphere C-18 reversed phase column (150 mm×4.6 mm) revealed a single peak with a retention time of 11.74 min (eluant: 10 mM tetrabutylammonium phosphate buffer, pH 7, 75%, acetonitrile, 25%; flow rate: 0.7 mL/min). $^1$H NMR (300 MHz, D$_2$O) γ 8.46 (s, 1H, C7-H), 7.41 (d, J=8.3 Hz, 2H, Ar), 6.34 (d, J=8.3 Hz, 2H, Ar), 4.24 (dd, J=4.4, 8.4 Hz, 1H, C19-H), 4.15 (s, 2H, C9-H$_2$), 3.53 (s, 4H), 3.47 (s, 2H), 3.42 (s, 2H), 3.18~2.97 (overlap, 14H), 2.28 (m, 2H, C22-H$_2$), 2.28~1.83 (m, 2H, C21-H$_2$). $^{13}$CNMR (75 MHz, D$_2$O) γ 178.9, 178.0, 175.9, 175.7, 173.6, 173.2, 169.0, 164.8 (C4), 154.4 (C2), 152.8 (C8a), 150.2 (C11), 148.3, 148.2, 128.9 (C13/15), 126.5 (C4a), 120.7 (C14), 111.7 (C12/16), 58.6, 58.2, 57.9, 55.6, 55.4, 51.9, 51.6, 51.1, 50.6, 45.4 (C9), 38.8 (C25), 38.5 (C26), 32.8 (C22), 28.1 (C21). High-resolution MS (Matrix Assisted Laser Desorption Ionization) C$_{35}$H$_{46}$N$_{12}$O$_{14}$ (MH$^+$) 857.830, found 587.853.

EXAMPLE 20

Radiotracer Synthesis:

The $^{111}$In-DTPA-folate radiopharmaceutical was obtained in high radiochemical yield by ligand exchange from $^{111}$In-citrate. Briefly, $^{111}$In$^{3+}$ (0.2–5.4 mCi) in Hcl (0.05 M; 2.55 μL) was transferred to a test tube and buffered by addition of 200 μL 3% aqueous sodium citrate. The resulting $^{111}$In-citrate was mixed with 300–350 μg DTPA-folate in water (2 mg/mL; pH 7–8). Two to 24 hours later, the radiochemical purity of ht e $^{111}$In-DTPA-folate was determined by TLC on C-18 reversed phase plates eluted with methanol and consistently found to exceed 98% ($^{111}$InDTPA-folate R$_f$=0.8; $^{111}$In-citrate R$_f$=0.0). The $^{111}$In-DTPA-folate product was diluted with normal saline, as needed, prior to use in the animal biodistribution experiments.

EXAMPLE 21

Cellular Uptake of $^{111}$In-DTPA-Folate:

Cultured KB and A549 cells in 35 mm dishes were incubated with 100 nM $^{111}$In-citrate or $^{111}$In-labeled DTPA-folate in 1 mL folate-deficient medium at room temperature for various lengths of time. The cells were then washed with 3×1 mL PBS and suspended in 1 mL PBS by scraping. The amount of cell-associated radioactivity was determined using an automatic gamma-counter. Cellular protein content was measured by the bicinchoninic acid assay. In folate competition experiments, the same protocol was used except that 1 mM folic acid was included in the incubation medium.

EXAMPLE 22

Biodistribution and Imaging Studies with $^{111}$In-DTPA-Folate:

All animal studies were carried out in accordance with procedures approved by the Purdue Animal Care and Use Committee. The biodistribution of $^{111}$In-DTPA-folate and $^{67}$Ga-DF-folate were determined I normal male Sprague-Dawley rats following intravenous injection under diethyl ether anesthesia, as described previously (Tsang et al., 1994). In addition, a gamma scintillation image of a female athymic mouse Nu/Nu (22 g) was obtained using a PhoGamma 37GP camera fitted with a 300 keV parallel hold collimator. The animal used for this imaging study was maintained for three weeks on folate-free diet (to reduce its serum folate to a level near that of human serum) and had been implanted subcutaneously in the interscapular region with human KB tumor cells. Tumor mass at the time of the imaging study was approximately 0.25 g. The animal was imaged 1 hour following intravenous administration of $^{111}$In-DTPA-folate (200 µCi in 0.1 mL) via the femoral vein under diethyl ether anesthesia. To promote clearance of radiotracer from the urinary bladder, 1.5 mL sterile saline was administered by i.p. injection immediately following he intravenous radiotracer injection. For imaging, the mouse was re-anesthetized with ketamine (60 mg/kg) and xylazine (6 mg/kg) immediately prior to the image acquisition period. Total administered mass of DTPA-folate conjugate was 13 µg (0.57 mg/kg).

Figure 3:
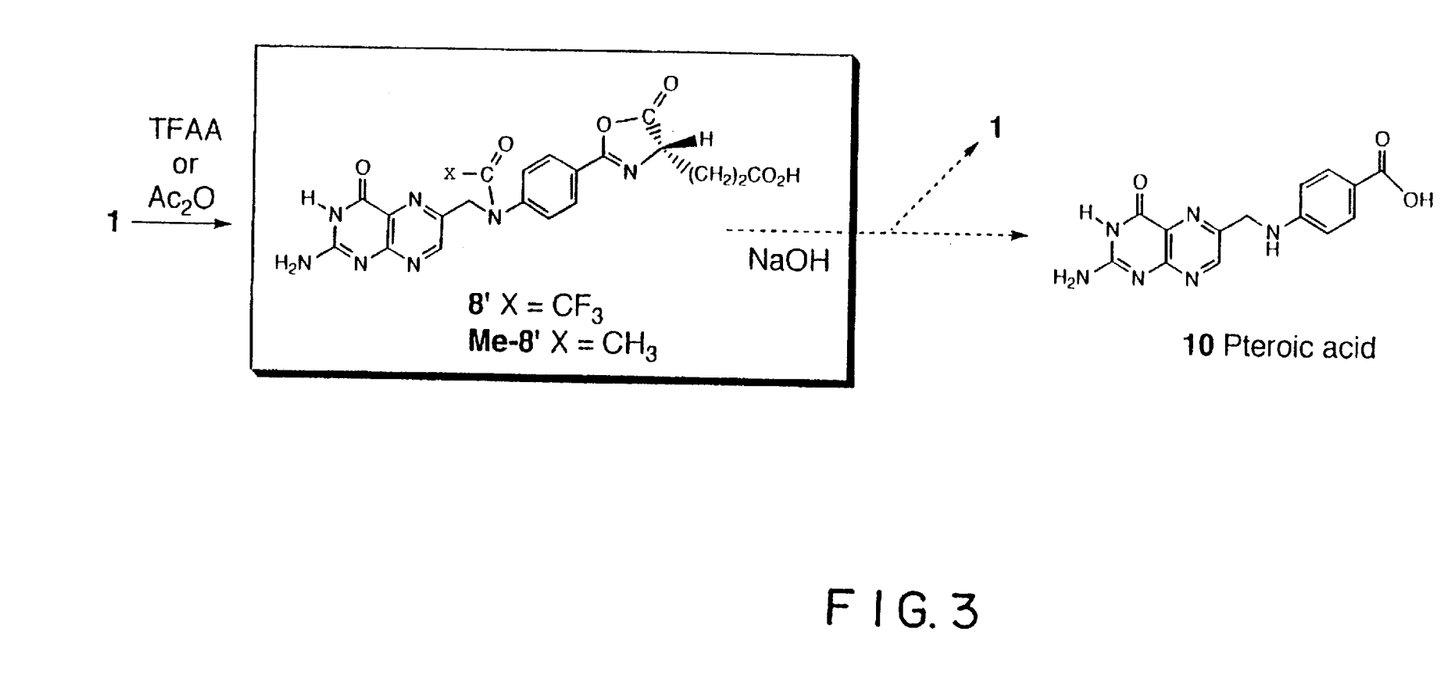
FIG. 3 depicts prior art teaching of reaction of folic acid and either acetic or trifluoroacetic anhydride.

Affinities of FITC-EDA-Folate for Cell Surface Receptors:

To determine the affinities of EDA-folate for cell surface folate receptors, the α- and γ-isomers were labeled with the fluorophore FITC and incubated with KB cells overexpressing the receptor. As shown in FIG. 3, 1.6 nM FITC-EDA-folate(γ) was required to reach 50% maximal binding, similar to that of folic acid and DF-folate(γ). Excess folic acid in the incubation medium effectively competed with the receptor binding of FITC-EDA-folate(γ). On the other hand, the α-isomer of FITC-EDA-folate had virtually no affinity for the cell surface receptors. The low level of non-specific uptake observed with both isomers was probably due to the hydrophobicity of the FITC conjugates.

What is claimed is:

1. A compound of the formula

I wherein Q is OH or NH$_2$, Y is hydrogen, nitroso, C$_1$–C$_4$ alkyl, C$_1$–C$_4$ alkanoyl, C$_1$–C$_4$ halosubstituted alkanoyl and Z is NHNH$_2$, or a group of formula provided that when Z is

Y is other than acetyl or trifluroacetyl.

2. A method of preparing a compound of the formula

II wherein Q is OH or NH$_2$, Y is hydrogen, nitroso, C$_1$–C$_4$ alkyl, C$_1$–C$_4$ alkanoyl, or C$_1$–C$_4$ halosubstituted alkanoyl, said method comprising the step of reacting a compound of formula

III wherein X is H or trifluroacetyl and Y' is hydrogen, C$_1$–C$_4$ alkyl, C$_1$–C$_4$ alkanoyl or C$_1$–C$_4$ halosubstituted alkanoyl, with hydrazine.

* * * * *